United States Patent [19]

Patel

[11] Patent Number: 5,254,473
[45] Date of Patent: Oct. 19, 1993

[54] SOLID STATE DEVICE FOR MONITORING INTEGRAL VALUES OF TIME AND TEMPERATURE OF STORAGE OF PERISHABLES

[75] Inventor: Gordhanbhai N. Patel, Somerset, N.J.
[73] Assignee: JP Laboratories
[21] Appl. No.: 494,572
[22] Filed: Mar. 16, 1990
[51] Int. Cl.⁵ .................... G01N 31/00; A22C 17/10
[52] U.S. Cl. .................................. 436/1; 436/2; 422/56; 422/57; 422/58; 422/82.12; 426/87; 426/88; 116/216
[58] Field of Search .............. 436/1, 2; 426/87, 88, 426/132, 418; 422/56, 57, 82.12, 58; 252/408.1, 962; 116/216

[56] References Cited

U.S. PATENT DOCUMENTS

| | | |
|---|---|---|
| 2,735,783 | 2/1956 | Tamblyn . |
| 3,290,499 | 12/1966 | Vale ................... 250/474.1 |
| 3,366,480 | 1/1968 | Gaynor . |
| 3,461,288 | 8/1969 | Oster ................... 250/474.1 |
| 3,743,846 | 7/1973 | Matsumoto ........... 250/474.1 |
| 3,845,662 | 11/1974 | Surgina et al. ........ 252/962 X |
| 3,899,677 | 8/1975 | Hori .................... 250/474.1 |
| 3,933,885 | 1/1976 | Satomura .............. 558/406 |
| 3,942,467 | 3/1976 | Witonsky ............. 422/119 X |
| 3,977,945 | 8/1976 | Tornmarck ............ 435/20 |
| 3,999,946 | 12/1976 | Patel .................... 422/56 |
| 4,001,587 | 1/1977 | Panchenkov .......... 250/474.1 |
| 4,065,430 | 12/1977 | Satomura .............. 526/193 |
| 4,154,107 | 5/1979 | Giezen et al. ......... 436/2 X |
| 4,238,352 | 12/1980 | Patel .................... 526/285 |
| 4,280,441 | 7/1981 | McNeely ............... 252/962 X |
| 4,675,161 | 6/1987 | Hashimoto et al. ... 436/2 |
| 4,698,296 | 10/1987 | Lewis ................... 430/333 |
| 5,045,283 | 9/1991 | Patel .................... 422/56 |
| 5,053,339 | 10/1991 | Patel .................... 436/2 |

FOREIGN PATENT DOCUMENTS

| | | | |
|---|---|---|---|
| 2742756 | 4/1979 | Fed. Rep. of Germany | 436/2 |
| 2077918 | 12/1981 | United Kingdom ........... | 436/2 |

OTHER PUBLICATIONS

Zall et al., Dairy and Food Sanitation, 6(7), 285-290 (1986) in FSTA 87: 2452.
Dahlig et al., Polimery (Warsaw) 31(6) pp. 211-213 (1986), in Chemical Abstract, 26, 228734q.
Pozdnyakovu, et al., Tr. Mosk. Khim.-Tekhnol. Inst. No. 61, pp. 237-240 (1969) in Chemical Abstract, 6, 26160j.
"Shelf-Life Dating of Foods"-T. P. Labuza, pp. 154,238 Food and Nutrition Press, Connecticut (1982).

Primary Examiner—Jill A. Johnston
Assistant Examiner—N. Bhat

[57] ABSTRACT

An indicator composition and process capable of changing color in relationship to its exposure to a temperature above and below a base line temperature and to the time of said exposure, for monitoring the time-temperature history of a substrate, depositable as a layer on said substrate, comprising a dispersion of either a binder comprising a reaction inert, neutral finely divided absorbent, in the presence of a reactant comprising a salt of an acid or an organic compound substituted by at least one moiety which, in ionic form, is an anion or a binder/reactant, comprising at least one solid organic polymer whose constituent units contain, as a covalent substituent, at least one moiety which, in ionic form, is an anion; as indicator, at least one acid sensitive pH dye and as activator, at least one base. This composition and process may be utilized to form a solid state device for monitoring integral values of time and temperature during storage of perishables. The device is a single solid indicating layer deposited upon a substrate. The time required for the color change and the activation energy of the device can be varied by varying the concentration and nature of reactants, catalysts, additives and polymeric binder/reactant matrix. The color change can be gradual or abrupt and exhibited as a continuous strip, as alphanumeric symbol(s) or as a line array which can be read by a bar code reader.

29 Claims, 3 Drawing Sheets

SOLID STATE DEVICE FOR MONITORING INTEGRAL VALUES OF TIME AND TEMPERATURE OF STORAGE OF PERISHABLES

BACKGROUND OF THE INVENTION

1. Field of the Invention

This invention relates to a solid state device for monitoring integral values of time and temperature of storage of perishables.

2. Brief Description of Prior Art

Perishable products such as fresh, refrigerated, and frozen, vegetables, fruits, meats, fish, poultry, dairy products, bakery products, juices, pre-cooked foods, soft and alcoholic beverages, and also including non-food items such as pharmaceuticals, vaccines, sera, blood, blood plasma, cosmetics, reactive chemical compounds, biochemical products, batteries, x-ray film and photographic films have measurable shelf-lives ranging from a few hours to some years, which are usually expressed within specified limits as the time left for available end use. The chemical kinetics of such reactions, including deterioration of perishables and devices to monitor this deterioration, can be determined with the Arrhenius equation:

$$\ln k = A - E_{act}/RT$$

where,

In k = natural logarithm of the reaction rate
A = pre-exponent constant
$E_{act}$ = activation energy
R = universal gas constant
T = absolute temperature in degrees Kelvin.

In order to be an effective device for monitoring the shelf life of a perishable, parameters such as the activation energy, rate, and order of deterioration of the perishable should be substantially identical to those of the device monitoring its thermal degradation.

A large number of time-temperature monitor (TTM) devices for monitoring thermal degradation of perishables have been reported in the patent literature. Many of these devices are based on diffusion of a chemical from one matrix to the other, sometimes through a barrier, to introduce color change in the indicator in the other matrix. For example, in U.S. Pat. Nos. 4,195,056 and 4,195,058, G. N. Patel describes a device based on diffusion of vapor through a barrier film to introduce color change in the indicator on the other side of the barrier. Giezen et al in U.S. Pat. No. 4,154,107 describe a device which utilizes an acid in a pressure sensitive adhesive which migrates to contact an organic dye producing an aqueous-mediated color change. Kydonieus et al in U.S. Pat. No. 4,212,153 describe a device in which a dye preferably migrates from a lower plastisol layer to an upper indicator layer. The device can also utilize a barrier film to introduce an induction period to color change. Bradley et al in U.S. Pat. Nos. 4,292,916 describe a tape device which involves the migration of a dye from a carrier layer to a transfer layer to highlight a message. U.S. Pat. Nos. 3,520,124 to Myers describes a device to indicate a predetermined time interval based on two or more materials which react, either chemically or physically over a predetermined period to produce a termination signal. The reacting materials are carried on a base member and are separated by a barrier preventing contact. Upon elimination of the barrier, a commencement signal is produced indicating the time reaction is underway.

Other patents in the art include: U.S. Pat. Nos. 3,677,088; 3,967,579; 3,360,338; 4,057,029; 3,065,083; 4,188,437; 2,889,799; 3,078,182; 3,311,084; 3,386,807; 4,154,107. Most of these devices require an activator, a compound which induces color change in the indicator, and an indicator which needs to be kept separate prior to use. None of the above patents describe a device in which, the operative reactant and indicator are present in one solid matrix/layer and undergo a color change with time and temperature.

In most TTM devices, especially those based on diffusion of chemicals, the color changing reaction occurs between an indicator (a dye) and an active compound (activator). This reaction is fast. However, in U.S. Pat. No. 3,977,945 (to S. Tornmarck) a device is described where the active compound is produced by a slow reaction between two chemicals, e.g. an enzyme reacting with a protein to produce a carboxylic acid which reacts with a pH dye sensitive to induce a color change. However, these types of reactions are carried out in solution. In the above example, two solutions, a solution of enzyme in one envelope and a solution of substrate and indicator in another envelope, are kept separate prior to use. The device is activated by breaking the barrier between the envelopes and mixing the solutions.

In U.S. Pat. No. 3,999,946, Patel et al describe a single layer TTM device based on the solid state polymerization of diacetylenes. Though, the rate of reaction can be varied by co-crystallization (U.S. Pat. No. 4,238,352), the activation energy of polymerization can not be varied significantly. Diacetylenes are expensive specialty compounds and they polymerize via first order reaction to blue or red colors only.

Further, radiation dosimeters are described in U.S. Pat. Nos. 3,899,677, 4,001,587, 3,743,846, and 3,461,288. Generally these dosimeters contain an acid sensitive pH dye dispersed in a chlorine containing polymer, e.g. polyvinylchloride, optionally a plasticizer, wherein the polymer releases HCl upon contacting with ionizing radiation and causes a color change in the dye. The color change is proportional to the amount of ionizing radiation and thus the device serves as a radiation dosimeter. However, the device is not described as being able to function in the absence of contacting ionizing radiation as a time-temperature history indicator.

Research is constantly being conducted for producing a TTM device in which all reactants and indicators for producing a color change are combined in a single solid matrix layer, are not expensive specialty chemicals, and which can react to produce a color change in the absence of contacting with ionizing radiation.

SUMMARY OF THE INVENTION

It has been unexpectedly found that many fast reactions which occur in the liquid state (solution or molten), e.g., deacidification of a polymer in the presence of a base, including dehydrohalogenation, can also be made to occur slowly in the solid state in a single layer solid matrix, by using a basic reagent. The increase in concentration of the acid products can be monitored with an acid sensitive pH indicating dye, which provides a noticeable color change.

The invention is directed to an indicator composition capable of changing color in relationship to its exposure to a temperature above and below a base line temperature and to the time of said exposure, for monitoring the time-temperature history of a substrate, depositable as a layer on said substrate.

This composition comprises a dispersion of either a binder comprising a reaction inert, neutral finely divided absorbent, in the presence of a reactant comprising a salt of an acid or an organic compound substituted by at least one moiety which, in ionic form, is an anion or a binder/reactant, comprising at least one solid organic polymer whose constituent units contain, as a covalent substituent, at least one moiety which, in ionic form, is an anion.

It further comprises as indicator, at least one acid sensitive pH dye and as activator, at least one base.

Suitably, in the composition, the binder/reactant or binder together with the reactant comprises between 10 and 90% w/w thereof, the indicator comprises between 0.001 and 10% w/w thereof, the activator comprises between 5 and 80% w/w thereof and is selected from at least one base. While strong bases may be used with certain binder reactants, it is generally preferred to use weaker bases, suitably those which as a 0.1% w/w/ aqueous solution, exhibit a pH of less than 8, to a total of 100% w/w.

Most suitably, the binder/reactant comprises between 30 and 70% w/w thereof, the indicator comprises between 0.02 and 5% w/w thereof and the activator comprises between 10 and 50% w/w thereof.

It is desirable that the compositions are capable of exhibiting a color change in the temperature range $-30°$ to $300°$ C., preferably a color change which is linear with time at the monitored temperature and possessing an activation energy to initiate said color change, of at least about 7 kcal/mole at the monitored temperature.

The invention is further directed to an indicator device capable of changing color in relationship to its exposure to a temperature above and below a base line temperature and to the time of said exposure, for monitoring the time-temperature history of a substrate, comprising a dispersion of a composition described above, deposited as a layer on said substrate. If desired the constituents of said layer are encapsulated in microcapsules activatable by applied pressure.

The said layer may be configured on said substrate to appear as a continuous strip, an alpha-numeric symbol, or as bar code group of lines readable by a bar code reader and may be placed on a package for a perishable product wherein the rate and nature of the color change is predetermined to have a direct relationship to the rate of decay of said perishable product. This provides a method of determining the elapsed shelf life of a perishable product by observing the color change of the device after storage.

BRIEF DESCRIPTION OF THE DRAWINGS/FIGURES

DESCRIPTION OF THE PREFERRED EMBODIMENTS

Figure 1:
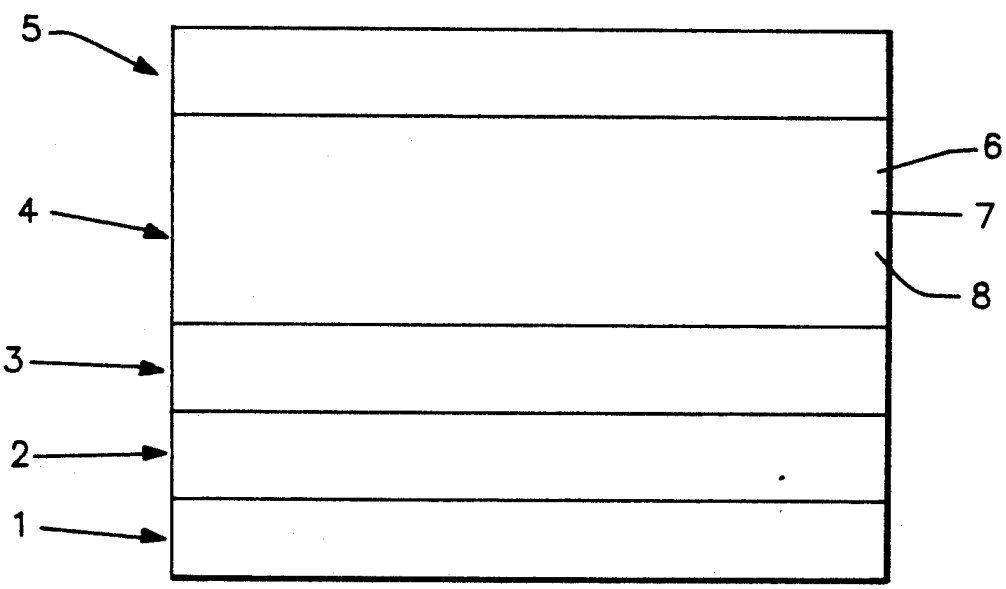
FIG. 1 is a schematic cross sectional view of the solid state time-temperature monitor.

In general, the device can be used to monitor perishables in the temperature range of $-30°$ C. (frozen foods) to $300°$ C. (oven foods) and preferably in the range of room temperature to $120°$ C. In general, the device can be used to monitor perishables in the time range of a few minutes to several years at room temperature or equivalent time at other temperatures.

As reaction inert binders, there may be used neutral earths such as clays, for example, kaolin talcs and the like, or neutral reaction inert polymers such as polystyrene, polyethylene, polypropylene, and the like.

The reactants may be the salts of organic or mineral oxides or substituents which, in ionic form, give anions such as specifically mentioned below.

The selection of polymeric binder/reactants for the devices includes any polymer, containing as a covalent the substituent of at least one moiety which in ionic form will provide the anion, which polymer can undergo a slow deacidification reaction to form the acid in the temperature region to be monitored and in which the concentration of product acid can be monitored with an acid sensitive pH indicator dye. Certain deacidification reactions are fast reactions and can not be used for this type of TTM device, because they will react during mixing, coating and drying. For example, hydrolysis of esters with strong bases are fast reactions. However, the rate of hydrolysis of esters decreases as strength of the base decreases. The rate of hydrolysis of cellulose nitrate is slow with primary and secondary amines and significantly slower with weak bases, e.g. tertiary amine such as triethanolamine and can be used with this device.

Similarly, another typical example is the dehydrohalogenation of halocarbons with a base. However, dehydrohalogenation of halocarbons, such as polyvinylchloride, requires relatively stronger base or higher temperature. The dehydrohalogenation of polyvinylchloride with a strong base such as sodium ethoxide and tetrabutylammonium hydroxide is relatively slow reaction at room temperature. The dehydrohalogenation of polyvinylchloride is very slow at room temperature. At higher temperatures, e.g. above $100°$ C., dodecylamine can initiate dehydrohalogenation of polyvinylchloride. Hence, with a strong base the dehydrohalogenation of halocarbons such as polyvinylchloride can be carried out at controllable slower rate at room temperature with a strong base and at a controllable slower rate with a weak base at higher temperature.

Preferred polymeric binder/reactants are those which are not significantly affected by ambient conditions such as light, air, air pollutants, and moisture and are nontoxic.

Reactive (acid producing) polymers which can be used in the invention include:

Polymeric materials, including oligomers (dimers, trimers, ... etc.) and copolymers, and their mixtures or alloys, having one or more of the following acid forming functionalities can be used as the polymeric reactant: F, Cl, Br, I, $SO_4$, $SO_3$, $SO_2$, $NO_2$, $NO_3$, $PO_4$, $PO_3$, $CO_2$, $CO_3$, CO—O—CO, $ClO_4$, $ClO_3$, $ClO_2$, $SbF_6$, $BF_3$, $AlCl_3$ and mixture thereof.

Especially suitable are Polymers including Polyvinylchloride, polyvinylidenechloride, halogenated polymers such as chlorinated polyethylene and polybutadiene, polychlorotrifluoroethylene, polychloroacrylate, starch-iodine complex, polyacrylonitrile, polynitropropylene, polynitrophenylene, polyvinylacetate, polyvinylcarbonate, polyacrylic anhydride, polymaleic anhydride, polyacrylates such as polymethylmethacrylate, polycyanoacrylate, polyesters such as polyethyleneterephthalate, polycarbonate of bisphenol A, polyurethanes, polyurea, polysulfones, polyvinylsulfoxide, polyvinylsulfate, esters of natural polymers such as cellulose nitrate, cellulose acetate, and cellulose acetate butyrate. particularly preferred are polyvinylchloride, cellulose nitrate, cellulose acetate butyrate and mixture thereof.

These reactive polymers may, if desired, be diluted with other additives in order to vary the activation energy and the time required for the color change some neutral materials/additives, organic or inorganic, can be added. These neutral materials could be low molecular weight materials, preferably those having melting point above room temperature, and polymeric materials which do not produce acid with interact with bases, suitably neutral matrix materials. These natural absorbents, for example, clays, neutral earths, silica gel, cellulose, natural filters and the like as well as synthetic matrix materials can be any polymeric materials in which the reactants can be dissolved or dispersed and, which, preferably provide or can be provided with transparent or translucent coating. General classes of polymers suitable for the matrix include homopolymers, and copolymers such as polyepoxy, phenol-formaldehyde and amino-formaldehyde resins, polyamides, polyvinyls, polyolefins, polyacrylics, polyurethanes, polyesters, water soluble resins, polyalkyds, natural and synthetic elastomers, polycarbohydrates such as cellulose and their derivatives, inorganic polymers such as polysilicones, polyethers, including those listed in "Handbook of Polymer Science", Bandrup, John Wiley and Sons, New York, 1989, "Resins for Surface Coatings", P. Oldring and G. Hayward, and "Resins and Varnishes for Ink and Paint", both published by McNair Publications, New York, N.Y., and mixtures thereof. By selecting the proper reactive polymers, additives, and diluents, the compositions can be made into an indicating layer in form of adhesive, e.g., pressure sensitive adhesive.

The binder may be separated from the reactant. The latter may include the low molecular weight materials such as inorganic and organic esters and carbonates, for example, sodium acetate, sodium carbonate, ethyltrichloroacetate, triglycerides of fatty acids, methyl cinnamate, methyl stearate, cetyl palmitate, phenyl stearate, dimethyl tartarate, phenyl benzoate, ethylene glycol dibenzoate, trimethylcitrate, diphenyl carbonate, dimethyl fumarate, pyrogallol triacetate, propyl butyrate, heptyl formate, benzyl acetate, and propyl benzoate.

Also included as reactants are halocompounds including chlorobutarldehyde, chlorophenols, ethylchloroacetate, chloroacetophenon, trichloroisopropanols, dichloroethylether, trichlorotoluene, hexachloroethane, chlorohexanes, bromoisobutaraldehyde, bromoethylacetate, tribromoethanol, iodobenzaldehyde, diiodobenzene, iodoform, and mixed halocarbons.

As the base activator which can be used in the invention, are suitably, compounds which exhibit a pH below 13 as a 0.1% aqueous solution are preferably a solid at room temperature and include low molecular weight or polymeric organic and inorganic materials, having one or more of the following functionalities: OH, $CO_3$ (carbonates), $PO_4$ (phosphate), $SiO_3$ (silicates), $CO_2$ (carboxylates), $BO_3$ (borate), $NH_2$, $NHR$, $NR_3$, (primary, secondary and tertiary amines) and polymeric bases such as polyethyleneimine and polyvinylpyridine.

Representative examples of strong base include inorganic hydroxides of alkali metals such as potassium hydroxide and organic hydroxides such as tetrabutylammonium hydroxide and sodium ethoxide. These however should only used with polymers or low molecular weight compounds having low reacting moieties, such as halo groups.

Representative examples of weak bases include salts of weak acids and strong bases such as metal carbonates including sodium carbonate and calcium carbonate, metal phosphates such as sodium phosphate and calcium phosphate, metal carboxylates such as sodium acetate, sodium citrate and sodium benzoate, metal silicates such as sodium silicate, metal borate such as sodium borate, organic amines including aliphatic, cyclic, and aromatic, primary, secondary and tertiary amines such as octylamine, dodecylamine, cyclohexylamine, aniline, N,N-dimethylaniline, diphenylamine, indole, piparazine, 4-aminoacetophenone, benzidine, amylamine, tetramethylenediamine, toludenes, triethanolamine, diethanolamine, zwitter ionic amines such as aminoacids occurring in nature and mixture thereof. Preferred bases are sodium carbonate, sodium acetate, dodecylamine, and polyethyleneimine.

Any compound which undergoes a noticeable color change in the presence of an acid can be used as an indicator. A typical class of such compounds are pH sensitive dyes. The acid sensitive pH indicator dye, useful in the present invention, is preferably solid at room temperature and undergoes color change when treated with acids such as acetic acid, hydrochloric acid or nitric acid. Desired color changes, e.g. red to green, green to red, and colorless to red, are obtained by selecting proper dyes or mixture of dyes.

In addition, many dyes normally do not change color with acids but they change colors with base. Dyes which change color with base also can be used because in the preparation of an indicator device, a base is added in the formulation. Thus the dye changes color. Production of acid will make the dye recover its color. Thus the dyes which undergo color change with base and acids can be used.

Some of the representative dyes which were tested in the system of polyvinylchloride and cellulose nitrate as binder/reactant and dodecylamine as activator as listed below:

Methyl Red, Ethyl Red, Methyl Red Na Salt, Methyl Red HCl, Metanill Yellow, Acid Blue 92, Eriochrome Black T, Phenylazoformic acid, Congo Red, Benzo Purpurin, Acid Blue 113, Acid Black 24, Acid Blue 120, Acid Red 151, Brilliant Crocein, Oil Red, Malachite Green Base, Alphazurine, Erioglaucine, Light Green SF, Alkali Fast Green 10GA, Pararosaniline Acetate, Pararosaniline Base, Pararosaniline Chloride, New Fuschin, Methyl Violet B Base, Methyl Green, Ethyl Violet, Acid Violet 17, Brilliant Blue G, Brilliant Blue R, Rosalic Acid, Bromothymol Blue, Chlorophenol Red, Pentamethoxytriphenylmethanol, Phenol Red, Phenolphthalein, Pyrocatechol, Tetrabromophenolphthalein, Thymol Blue, Victoria Blue B, Resazurin, Acid Blue 45, Dichloroindophenol-Na salt, Diphenycarbazide, Leucoquinizarin, and Curcumin.

The selection of dye depends upon the need for the color change required. For example, the preferred dyes and color changes are listed below:

| Name of Dye | Color Original | Change Final |
|---|---|---|
| Methyl Red | Yellow | Red |
| Chrome Azurol S | Yellow | Red |

| Name of Dye | Color Original | Change Final |
|---|---|---|
| Rosalic Acid | Red | Yellow |
| Brillant Yellow | Red | Yellow |
| Eriochrome Black T | Blue-Green | Red |
| Bromocresol Purple | Violet | Yellow |
| Xylenol Orange | Purple | Yellow |
| Neutral Red | Yellow | Red |
| Dichloroindophenol | Blue | Red |
| Acid Blue 113 | Blue | Green |
| Malachite Green | Colorless | Green |
| Parosaniline Base | Colorless | Red |
| Paraosaniline Chloride | Colorless | Red |
| Brilliant Blue G | Yellow | Green |
| Pentamethoxytriphenyl MeOH | Colorless | Yellow |
| Tetrabromophenolphthalein | Colorless | Yellow |
| Victoria Blue B | Light Red | Light Blue |

For example, colorless to red one may use pararoseaniline and for colorless to green one may use malachite green. In order to get desired color often one has to use a mixture of more than one dye. For example, for green to red color change one may use mixtures of malachite green and rosalic acid, and for green to red one may use eriochrome black T and neutral red.

The device and its performance can best be described by reference to the FIG. 1. The device is made by preparing an indicating layer 4, composed of a polymeric binder/reactant 6, acid sensitive pH indicator dye 7 and weak base activator 8 dissolved or dispersed in the solid polymeric binder/reactant indicating layer 4, deposited on a substrate 3. The indicating layer 4 may have a top layer 5 and the substrate 3 may have an adhesive layer 2 with a release backing 1.

The reactants, i.e., the polymeric binder/reactant 6, the base activator 8, and the acid sensitive pH indicator dye 7, either do not react or react slowly in liquid (solution or molten) state. The reactants can be mixed and coated on a substrate 3 to make the device without introducing significant color change. Once the coating is dried, the reactants react at a controlled rate. The rate, order and activation energy of the reaction, and hence that of the color change, is controlled by controlling one or more of parameters such as concentration and nature of (1) indicators, (2) reactants, (3) catalysts, (4) matrices, and (5) diluent or additives.

The substrate 3 can be any solid material such as paper, plastics and metals, on which a reaction mixture can be applied uniformly with good adhesion. The substrate can be thin and flexible or can be a rigid container suitably for a perishable. Representative examples include a large number of plastic films including those made from polyethylene, polypropylene, cellulose derivatives such as cellulose acetate, polyesters such as poly(ethylene terephthalate), polyamides such as nylon-66, polyurethanes, polyvinylchloride, and polycarbonates such as poly(bisphenol-A carbonate). Preferred substrate films are polyethylene, polypropylene, cellulose acetate, poly(ethylene terephthalate), polyvinylchloride and multi-layer laminated films, preferably comprising a composite of polyethylene, polyethylene terephthalate, polyvinylchloride, metal foils such as aluminum and synthetic and natural paper. If the substrate is transparent, the coating can be made reflective by adding fine particles of an additive such as silica and alumina.

The flexible substrate can also be coated with an adhesive and release coat/paper on the other side of the indicating layer. Once the film is coated with the indicating layer, the device is applied to the perishable container by removing the release paper.

The top coating should be substantially transparent, and should substantially prevent/minimize diffusion of reactive chemicals (chemicals which react mainly with the reactant or affect the rate/nature of reaction) in the atmosphere and effect of other ambient conditions such as humidity, ultraviolet light, and pollutants. The top coat can be coated from solution/emulsion or laminated. The binder material can also be a top coat.

Representative examples of the top coating are synthetic polymers such as polyethylene, polypropylene, polyesters, polydienes, polyvinylacetate, polyurethane, polyamides, polyethyleneglycol, polystyrenes, polyacrylates, polymethacrylates, polyacrylamides, polyvinyl esters, polyoxides, polycarbonates, polyvinylchloride, polysiloxanes, and natural polymers such as derivatives of cellulose and starch and gelatin and mixture thereof.

The mixture for the device is prepared by mixing the composition of this invention containing at least one indicator and at least one solid binder and a reactant or a binder/reactant matrix, dispersed or dissolved in a suitable solvent. The indicator layer is prepared by making a dry layer on a support, which can preferably be achieved by coating the indicating-mixture on a plastic film or a perishable container followed by drying. The drying, preferably, is done at low temperature, e.g. room temperature, by blowing air or removing solvent under vacuum. For quick drying of the indicating layer, one can use highly volatile liquids. Alternatively, one can used UV curable monomers and oligomers as the matrix.

The TTM device can be prepared by printing from ink which is more convenient. Useful herein are a variety of inks such as flexo, gravure, off-set, letter press, and litho which are used for printing. Inks are composed of three basic components, vehicle (solvent), pigment (color) and binder (polymer). The ink (matrix) for the device can be composed of the similar three basic ingredients, reactants, (pigment), solvent (vehicle) and matrix (binder) such as cellulose nitrate, rosin esters, acrylate and vinyl polymers, polyesters, polyamides and polyepoxy.

The device can also be prepared by coating the compositions directly onto a container for perishable products, for example, by printing with the mixture. When solvent evaporates the device/coating becomes active. The coating can suitably be applied at the time of filling the container with the perishable.

Another modification of the device of FIG. 1 is to coat or print the indicating-mixture of the reactants (which can be in the form of an ink, paint, solution or lacquer) in the form of a message. Instead of the continuous coating, one can coat or print the mixture in form of a message, e.g. IF THIS IS RED, DO NOT USE. In such case, only the message will gradually appear or undergo the color change.

Another modification of the invention is to coat or print the mixture in form of bar codes. Instead of the continuous coating of TTM, one can coat or print TTM in form of a bar code. In this case, only the bars or the background will undergo the color change and a conventional bar code reading apparatus can be used to read shelf life of the perishable. Other product information, such as inventory control and price, can also be combined into the bar codes. As the bar code reader read only dark (blue or black) colors, one can select proper color change for the acceptance or rejection of the perishables by the bar code reader. To decode the information in a bar code, a small spot of light is passed over the bars and spaces via a scanning device. The bar code will reflect the light back into the scanner in various amounts. These differences in reflections are translated into electrical signals by a light detector inside the scanner. The signals are converted into binary zeroes and ones which are used in various combinations to stand for specific numbers and letters.

The device can be prepared in form of big rolls and stored at low temperature to stop or slow down the reaction. The roll can subsequently be loaded onto a particular processing machine/equipment. The device is cut to the desired size and applied to the perishable. Commercially available equipment for application of labels which are conventional can be combined and modified for application of the device on line.

The size of the device can be as small as a few millimeters to several centimeters or larger, if desired. The thickness of the device typically can be from a ten-thousandth of a centimeter to a millimeter, or thicker, if desired.

The device can be prepared by coating the mixture on a flexible substrate. Coating is an old and well developed technology. A variety of processes/equipment have been developed for coating adhesives, inks, lacquers, solutions, and other polymeric materials. Common coating methods are: air knife, brush, colander, cast coating, curtain, dip, extrusion, blade, floating knife, gravure, kiss roll, off-set, reverse roll, rod, spray, and squeeze roll. These methods have been reviewed by Coeling, and Bublick (K. J. Coeling, and T. J. Bublick, Encycl. Polym. Sci. Eng., Vol. 3, 552-615, 1986). Most of the above methods can be used for coating the mixture on a wide range of base materials.

Unless specific steps are taken, the TTM device become active when coated on a substrate. However, one can prepare an inactive device which can be activated when ever desired by special means. Such inactive device can be prepared by using reactants which normally do not react, and reactive reactants are produced by giving special treatment/means such as pressure or irradiation. If a reactant is microencapsulated, it can be released by applying pressure. If the activator can be decomposed by radiation, the assembled device can be activated by radiation (see "Effect of Radiation on Materials and Components" by J. Kircher and R. Bowman (Ed.). Reinhold Publishing Corp., N.Y. and "Radiation Effects in Materials". Vol. 2, A. Charlesby (Ed.) Pergamon Press, N.Y.).

Though first and higher order reactions can be used for perishables having such reactions, the desired reaction is the zero order reaction, in which the color change of the indicator dye is linear with respect to time at the temperature of monitoring. One of the methods of making a reaction zero order, is to significantly increase concentration of the reactants.

The TTM devices preferably have a low activation energy, e.g. below about 7 kcal/mole for use as a time indicator. The effect of temperature on time required for the color change of the device will decrease as the activation energy decreases. At low activation energy the TTM device becomes a time indicating device. If temperature is kept constant or varied within a narrow range, a TTM is essentially a time indicator.

The time required for color change depends upon temperature. For example, a device made from cellulose nitrate, dodecylamine and malachite green base requires about a month to develop a green color. However, if heated with hot air blower (above 150° C.), the device develops the green color in a few seconds. Thus, TTM device becomes a temperature indicating device.

The preferred concentrations of binder/reactant, pH sensitive dye and base activator will depend upon their molecular weight and functional groups. For example, cellulose nitrate having 2.5 nitrate groups is expected to be 2.5 time more effective than that having 1 nitrate group per repeat unit. Similarly, a base having two $-NH_2$ functionality per molecule will be twice effective compared to molecule having one primary group.

The preferred concentration of additive/diluent is 1 to 90 weight percents and the most preferred concentration of the additive/diluent is 5 to 30 weight percent of the indicating layer.

The preferred thickness of the indicating layer is 1 micron to 1 millimeter and the most preferred thickness of the indicator layer is 10 to 100 microns.

Representatives of the most preferred embodiments of the composition are the following:
cellulose nitrate or polyvinylchloride with polyethyleneimine, dodecylamine, or sodium carbonate in the presence of Malachite green, pararoseaniline, rosalic acid, eriochrome black T, and methyl red. These yield, as preferred, color changes: Colorless to red, colorless to green, red to green to yellow to red, and vice versa.

EXAMPLES

The following examples are illustrative of carrying out the claimed invention but should not be construed as being limitations on the scope or spirit of this invention.

Method A. General Method of Preparation of Coating Mixture

In a 5 ml test tube were added 0.5 ml of about 2% solution of an indicator, 0.2 ml of about 20% solution of an activator and 2 ml of about 10% solution of a binder and/or reactant. The mixture was stirred to form uniform solution or dispersion.

Method B. General Method of Preparation of the Devices

Devices were prepared by coating the mixture on 4 ml polymer sheets (suitably Mylar) using 3 mil bar (a wet film applicator) and allow to dry under ambient conditions. The solvent, being volatile, evaporated in a few minutes. The samples were stored at $-20°$ C. prior to use. The solutions were also coated on Mylar with wire wound rods and gravure rollers.

Method C. Measurement of Reaction

The extent of reaction was determined by monitoring color either visually or with an instrument such as spectrophotometer. A piece of film was placed on a metallized Mylar sheet. Visible spectra were recorded in reflectance mode using a fiber optic UV-visible spectrophotometer, Guided Wave Model 150 at different time. For some samples, the absorbance at various predecided wavelengths was collected and printed using a printer.

Method D. Effect of Temperature and Determination of Activation Energy

The device was placed in an oven at different temperatures and spectra and/or change in absorption were recorded at different times for different temperatures ranging from RT to 130 degree centigrade. For low temperature spectra were recorded by storing samples for different periods of time.

Figure 2:
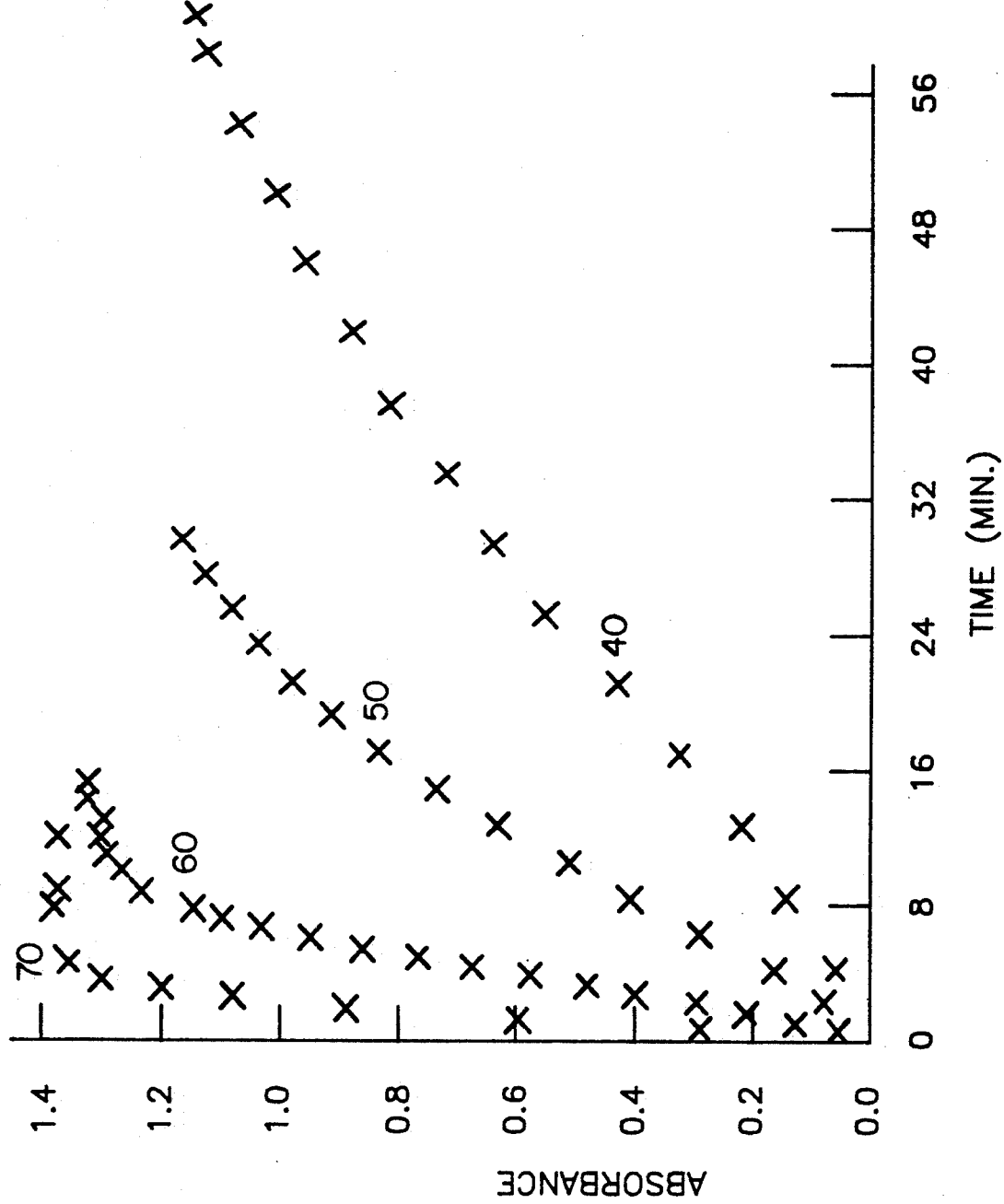
FIG. 2 is a plot of absorbance versus time for the TTM of Example 2 at various temperatures (oC).
Figure 3:
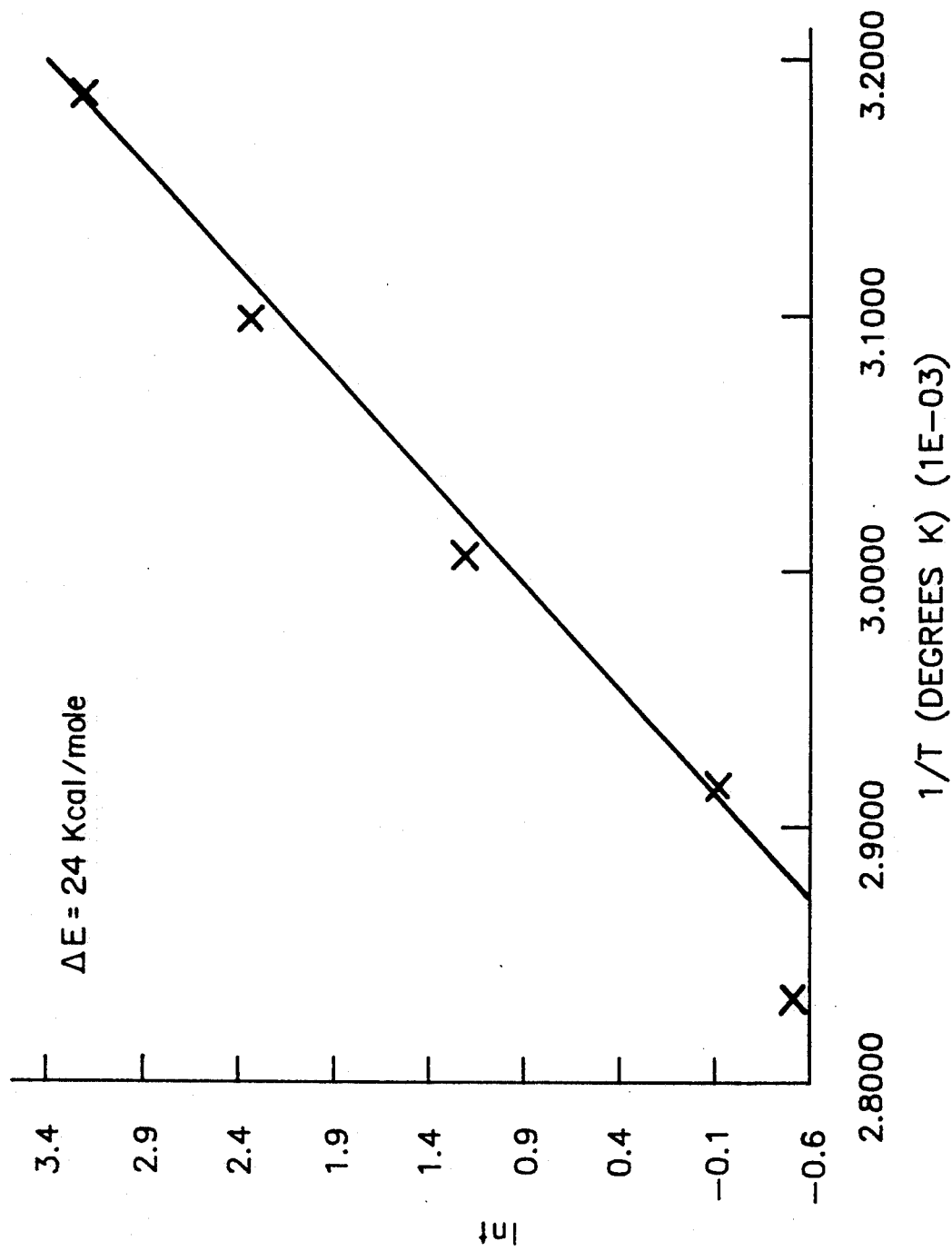
FIG. 3 is a Arrhenius plot (logarithm of t½ versus 1/T) for the TTM of Example 2.

The absorbance values were plotted against time for different temperatures. A plot of Absorbance versus Time (Example 2) is shown in FIG. 2 for TTM made from cellulose nitrate as binder/reactant, dodecylamine as activator and malachite green base as an indicator. The reaction is zero order reaction, i.e. development of the color (absorbance) is linear with time. Time required to reach 50% of the reaction (50% of the absorbance),t ½, was noted for each temperature from the plots of absorbance versus time. Arrhenius plot of In t½ versus reciprocal of absolute temperature (K) was plotted for each system. The Arrhenius plot for data of Example 2 is shown in FIG. 3.

As seen from the data in FIG. 2, the reaction is zero order, that is, color change is linear with time for major fraction of reaction. A large number of perishables degrade by zero order reactions. Hence, time-temperature indicators having zero order reaction kinetics are more desirable and reliable for perishables that degrade by zero order reaction.

EXAMPLE 1

Cellulose Acetate Butyrate as Binder and Reactant

About 10 mg of some selected dyes (which change color with carboxylic acid) were shaken in a 5 ml test tubes. 1 ml of 5% solution of cellulose acetate butyrate in methylethylketone was added and stirred to make solution. To the mixture was added 0.25 ml of 30% solution of dodecylamine in methylethylketone, stirred and coated on 4 mil Mylar following Method B. The pieces of the coated films were store at room temperature and at 60° C. and color changes were noted. The results are summarized in Table 1 for some dyes after 21 days at room temperature and after 8 hours at 60° C. The control samples (coatings prepared without dodecylamine did not change color) under identical thermal annealing.

TABLE 1

Color change of time-temperature indicating devices made from cellulose acetate butyrate, pH dye and dodecylamine.

| Name of Dye | Original Color | Color after Annealing RT (21 day) | Color after Annealing 60° C. (8 hour) |
|---|---|---|---|
| Brilliant Green | Colorless | Green | Green |
| Methyl Green | Colorless | Violet | Violet |
| Acid Fuschin | Colorless | Magenta | Magenta |
| Alkali Blue 6B | Colorless | Blue | Blue |
| Chlorophenol Red | Purple | Colorless | Colorless |
| a-Naphtholbenzein | Blue-Green | Ash | Yellow |
| Thymol Blue | Green | Yellow | Yellow |
| Gallocyanine | Colorless | Violet | Blue |

Thus, polymeric materials which can undergo at least one reaction with activator, e.g. de-esterification of cellulose acetate butyrate with amine, can be used as reactant/binder for preparation of time-temperature indictors. The reaction can be monitored with a variety of indicators, e.g., formation of acids with a pH dye.

EXAMPLE 2

Cellulose nitrate as Binder/Reactant and effect of Plasticizer/Neutral Additives The TTM devices were prepared by coating the following solutions using the coating procedure described in Method B:

| | |
|---|---|
| Cellulose nitrate (SS½ obtained from Hercules, Inc) = | 2 ml, 20% in 2-butanone (MEK) |
| Malachite green base = | 0.25 ml, 5% in MEK |
| Dodecylamine = | 1.0 ml, 30% in MEK |
| Camphor (plasticizer) = | 0.14 g |

The color change of the devices was monitored at different temperatures using the procedure described in Method C. The plots of absorbance versus time were linear for almost 80-90% of the reaction as shown in FIG. 2. The time required for 50% of the reaction is noted in the following Table 2:

In accordance with the above procedure a dodecylamine range of 0.1-1 ml in 30% MEK is operative.

TABLE 2

Time required for color change for cellulose nitrate-dodecylamine system.

| Temp (° C.) | t½ (min) |
|---|---|
| 40 | 23.0 |
| 50 | 10.5 |
| 60 | 3.4 |
| 70 | 0.9 |
| 80 | 0.6 |
| 92 | 0.17 |

The activation energy of the device as determined according to procedure described in Method D was 24.5 kcal/mol. When dioctylphthlate was used as the plasticizer, the activation energy of the device was 25.5 kcal/mol. When no plasticizer was used the activation energy of the device was 22 kcal/mole. When hexadecylamine was used as the activator the activation energy was 28.8 kcal/mol.

It was also found that the activation energy as well as the time required for the color change can be decreased by decreasing the concentration of the amine and increased by increasing the concentration of amine. However, no color change was observed when significant excess of amine, especially polyethyleneimine was used.

It was also found that the time required for the color change can be varied by adding neutral additives including polymeric diluents such as polyethylene glycol, polyethylene oxide, polycaprolactone, and polyvinylacetate.

Some of the above devices were top coated with polymers such as polybutadiene, polystyrene, polyvinylchloride, polycaprolactone, polyvinylacetate and cellulose acetate butyrate.

EXAMPLE 3

Polyvinylchloride as Binder/Reactant

The devices were prepared by coating the following solution using the coating procedure described in Method B:

| | |
|---|---|
| Polyvinylchloride = | 5.0 ml, 4% in Tetrahydrofuran (THF) |
| Malachite green base = | 0.5 ml, 5% in MEK |

-continued

| Dodecylamine = | 1.0 ml, 30% in MEK |
|---|---|

The color change of the devices was monitored at different temperatures using the procedure described in Method C. The plots of absorbance versus time were linear for almost 80-90% of the reaction. The time required for 50% of the reaction is noted in the following Table 3:

TABLE 3

Time required for color change for polyvinylchloride-dodecylamine system.

| Temp (° C.) | t½ (min) |
|---|---|
| 39.5 | 39.0 |
| 49.4 | 10.0 |
| 59.1 | 2.75 |
| 68.5 | 0.675 |

The activation energy of the device as determined according to procedure described in Method D was 28.8 kcal/mole.

Thus, the device is not limited to de-esterification. It can be used for most of the slow reactions as shown in this example for dehydrohalogenation of polyvinylchloride.

The activation enery as well as the time required for color change was varied by varying the nature and concentration of low molecular weight and polymeric additives.

EXAMPLE 4

Low Molecular Weight Organic and Inorganic Compounds as Reactants

A small quantity (about 20 mg) of malachite green was dissolved in 4 ml of 3% solution of poly(ethyleneimine) in water/methanol (1:9). A colorless solution was obtained. About 0.5 gram of isopropylnitrate was added in the solution and coated on Mylar film. The coating was colorless. When heated to high temperature with hot air or in an oven, the coating turned green. Similar results were obtained when isopropylnitrate was replaced with potassium nitrate and ammonium nitrate.

The above results indicate that low molecular weight, organic and inorganic reactants can be used. The activator can be polymeric. In case of low molecular weight reactants and activators, one may need to use a neutral polymeric binder.

EXAMPLE 5

Low Molecular weight reactants

A solution of 0.2 gram of glyceroltriacetate, 0.2 gram of docecylamine, 0.01 gram of bromophenol blue and 0.5 gram of polyethyleneglycol were dissolved in 5 ml of methanol. The solution was coated on a Mylar film using the procedure described in Method B. A blue colored coating was obtained. The coating turns orange when heated in oven at 60° C.

EXAMPLE 6

Microwave Food Readiness Indicator

The TTM devices were prepared by coating the following solutions using the coating procedure described in Method B:

| Polyvinylchloride = | 5.0 ml, 6% in MEK |
|---|---|
| Malachite green base = | 0.5 ml, 4% in MEK |
| Rosalic acid = | 0.5 ml, 4% in MEK plus dodecylamine to dissolve the dye |
| Dodecylamine = | Varied from 0.2 to 2.0 ml, 20% in MEK |
| Additives (e.g. polycaprolactone) = | 0.25-2 ml, 9% solution in chloroform |

Pieces of the red color TTM devices prepared from the above mixtures were attached to a beaker containing water, a beaker containing ethylene glycol, and microwave food packages (e.g., microwaveable cheese enchiladas and pizza) and placed in microwave oven. The oven was turn on. Depending upon concentration of amine and additives, the pieces turned red to green. In general, higher concentration of additives such as polycaprolactone, decrease the time required for the color change.

EXAMPLE 7

Use of a Strong Base

The TTM devices were prepared by coating the following solutions using the coating procedure described in Method B:

| Polyvinylchloride = | 2.0 ml, 6% in MEK |
|---|---|
| Malachite green base = | 0.5 ml, 4% in MEK |
| Tetrabutylammonium Hydroxide (TBAH) = | 1 to 10 drops of 26% in methanol |

Pieces of the TTM devices prepared from the above mixtures were annealed at 60° C. The time required for the device to develop green color is listed in table 4:

TABLE 4

Effect of Concentration of Tetrabutylammonium hydroxide

| Concentration of TBAH in film (% w/w) | Color at RT after six hours | Time to become dark green at 60° C. (Minutes) |
|---|---|---|
| 4 | Colorless | light green after 6 hours |
| 8 | Pale yellow | Green after 6 hours |
| 12 | Light yellow | 300 |
| 16 | Pale green | 55 |
| 20 | Light green | 13 |
| 24 | Green | 10 |
| 28 | Green | 7 |
| 32 | Green | 5 |

I claim:

1. A method of determining the elapsed shelf life of a perishable product comprising the steps of (1) packaging said product with an indicator device capable of changing color in relationship to its exposure to a temperature above and below a base line temperature and to the time of said exposure, for monitoring the time-temperature history of a substrate, comprising a solid state dispersion comprised of:
   (a)(i) a binder comprising a reaction inert, neutral finely divided absorbent, in the presence of a reactant being a salt of an acid or an organic compound substituted by at least one labile moiety which, in ionic form, is an anion or
   (ii) a binder/reactant, comprising at least one solid organic polymer whose constituent units contain, as a covalent substituent, at least one labile moiety which, in ionic form, is an anion;

(b) as indicator, at least one acid sensitive pH dye which is non-phototropic during the time of said exposure, (c) as activator, at least one base, deposited as a layer on said substrate; and (2) observing the color change of the device after storage.

2. A method of claim 1 wherein (a) the binder/reactant comprises between 10 and 90% w/w thereof, (b) the indicator comprises between 0.001 and 10% w/w thereof, (c) the activator comprises between 5 and 80% w/w thereof and is selected from at least one weak base, which as a 0.1% w/w aqueous solution, exhibits a pH of less than 8, to a total of 100% w/w.

3. A method of claim 1 wherein (a) the binder/reactant comprises between 30 and 70% w/w thereof, (b) the indicator comprises 0.02 and 5% w/w thereof, (c) the activator comprises between 10 and 50% w/w thereof, to a total of 100% w/w.

4. A method of claim 1 wherein said indicator exhibits exhibiting a color change in the temperature range $-30°$ to $300°$ C.

5. A method of claim 1 wherein said color change is linear with time at the monitored temperature.

6. A method of claim 1 wherein said indicator possesses an activation energy to initiate said color change, of at least about 7 kcal/mole at the monitored temperature.

7. A method of claim 1 wherein said covalent substituent of said polymeric binder/reactant is, in ionic form the anion of a mineral acid.

8. A method of claim 1 wherein said covalent substituent of said polymeric binder/reactant is, in ionic form the anion of an organic acid.

9. A method of claim 1 wherein said polymeric binder/reactant is selected from the group consisting of: polyvinylchloride, cellulose nitrate, and cellulose acetate butyrate.

10. A method of claim 1 wherein said activator is selected from the group consisting of salts of weak acids, salts of strong bases, primary, secondary and tertiary amines, quaternary ammonium salts, polymeric amines and polymeric imines.

11. A method of claim 10 wherein said activator is selected from the group consisting of: dodecylamine, polyethyleneimine, and potassium carbonate.

12. A method of claim 1 wherein said dye is selected from the group consisting of: Malachite Green, Rosalic acid, eriochrome black T, methyl red and mixtures thereof.

13. A method of claim 1 wherein said binder/reactant is cellulose nitrate and said activator is dodecylamine.

14. A method of claim 1 wherein said binder/reactant is polyvinylchloride and said activator is dodecylamine.

15. A method of claim 1 wherein said binder/reactant is polyvinylchloride and said activator is polyethyleneimine.

16. A method of claim 1 wherein said dye is a mixture of Malachite Green and Rosalic acid.

17. A method of claim 1 wherein said indicator device further comprises a substantially transparent substantially diffusion blocking top coating.

18. A method of claim 17 wherein the substantially transparent substantially diffusion blocking top coating is a natural or synthetic polymer.

19. A method of claim 1 wherein said layer on said substrate a continuous strip, an alpha-numeric symbol, and as a bar code group of lines readable by a bar code reader.

20. A method of claim 1 wherein said substrate is a package for a perishable product.

21. A method of claim 1 wherein said substrate is a package for a perishable product and the rate and nature of the color change is predetermined to have a direct relationship to the rate of decay of said perishable product.

22. A method of claim 21 wherein said substrate is a package for a perishable product said package containing said product and the rate and nature of the color change is predetermined to have a direct relationship to the rate of decay of said perishable product.

23. A method of claim 1 wherein said temperature to be monitored is in the range room temperature to 120 degrees C.

24. The method of claim 1 wherein said device is capable of exhibiting a color change in the temperature range of room temperature to 120 degrees C.

25. The method of claim 1 wherein said color change is linear with time at the monitored temperature.

26. The method of claim 1 wherein said binder/reactant is polyvinylchloride, said activator is dodecylamine and said dye is a mixture of malachite green and rosalic acid.

27. The method of claim 1 wherein said binder/reactant is cellulose nitrate, said activator is dodecylamine and said dye is a mixture of malachite green and rosalic acid.

28. The method of claim 1 wherein said composition dispersion is encapsulated in a microcapsule.

29. The method of claim 1 wherein said indicator device changes color in relationship to its exposure to a temperature above and below a base line temperature and to the time of said exposure for monitoring the time-temperature history of a substrate comprising a dispersion of polyvinylchloride, dodecylamine, malachite green and rosalic acid deposited on a layer on a substrate.

* * * * *